United States Patent
Styrc (10) Patent No.: US 9,427,317 B2
(45) Date of Patent: Aug. 30, 2016

(54) DEVICE FOR TREATING A BLOOD CIRCULATION CANAL AND PROCESS FOR PREPARING THIS DEVICE

(75) Inventor: Mikolaj Styrc, Kopstal (LU)

(73) Assignee: CORMOVE, Bornel (FR)

( * ) Notice: Subject to any disclaimer, the term of this patent is extended or adjusted under 35 U.S.C. 154(b) by 1307 days.

(21) Appl. No.: 11/730,699

(22) Filed: Apr. 3, 2007

(65) Prior Publication Data

US 2007/0233223 A1  Oct. 4, 2007

(51) Int. Cl.
*A61F 2/06* (2013.01)
*A61F 2/24* (2006.01)
*A61F 2/95* (2013.01)
*A61F 2/07* (2013.01)

(52) U.S. Cl.
CPC .............. *A61F 2/2439* (2013.01); *A61F 2/95* (2013.01); *A61F 2/07* (2013.01); *A61F 2002/9511* (2013.01)

(58) Field of Classification Search
CPC ........... A61F 2/06; A61F 2/95; A61F 2/2439
USPC ................................................ 623/1.11, 1.12
See application file for complete search history.

(56) References Cited

U.S. PATENT DOCUMENTS 5,554,183 A * 9/1996 Nazari ........................ 623/1.49
5,713,948 A * 2/1998 Uflacker ..................... 623/1.23
5,800,506 A 9/1998 Perouse
6,821,291 B2 * 11/2004 Bolea et al. ................. 623/1.11
7,942,921 B2 * 5/2011 Nissl et al. .................. 623/1.15
2001/0018574 A1 * 8/2001 Toledo et al. ............ 604/164.09
2003/0050684 A1 * 3/2003 Abrams et al. ............. 623/1.11
2005/0119722 A1 * 6/2005 Styrc et al. ................. 623/1.12
2008/0243225 A1 * 10/2008 Satasiya et al. ............ 623/1.12

FOREIGN PATENT DOCUMENTS

| CA | 2213291 | 2/1998 |
| EP | 0 829 242 | 3/1998 |
| EP | 829242 A1 * | 3/1998 |
| FR | 2 865 926 | 8/2005 |
| FR | 2 874 812 | 3/2006 |

* cited by examiner

*Primary Examiner* — Richard Louis
(74) *Attorney, Agent, or Firm* — Wenderoth, Lind & Ponack, L.L.P.

(57) ABSTRACT

This device includes a hollow support delimiting, in the vicinity of a distal end, a transverse retention opening. It further includes an endoprosthesis which can be deployed between a state retracted against the support and an expanded state. The device further includes a filamentary connection forming a clamping ring surrounding the endoprosthesis and forming a loop engaged in the support through the retention opening. A retention rod mounted to be movable in the support, and the retention rod has a hook for retaining the loop. The displacement of the retention rod from a release position to a retention position brings about the tightening of the clamping ring.

16 Claims, 5 Drawing Sheets

DEVICE FOR TREATING A BLOOD CIRCULATION CANAL AND PROCESS FOR PREPARING THIS DEVICE

TECHNICAL FIELD

The present invention relates to a device for treating a blood circulation canal, of the type including a hollow support delimiting, in the vicinity of a distal end, at least one transverse retention opening; an endoprosthesis which can be deployed between a state retracted against a lateral surface of the support and an expanded state in which the endoprosthesis can be released from the support; at least one filamentary connection forming a clamping ring surrounding the endoprosthesis and forming a loop engaged in the support through the retention opening. The clamping ring extensible between a configuration for maintaining the endoprosthesis in its retracted state and a configuration for deploying the endoprosthesis. For each filamentary connection, a retention rod is mounted to be movable in the support between a position for retaining the loop and a position for releasing the loop.

Such a device is used for releasing in a blood circulation canal endoprostheses of the type commonly referred to by the term "stent", or endoprostheses of the endovalve type comprising a stent and a valve secured to the stent.

BACKGROUND OF THE INVENTION

A device of the above-mentioned type is described in EP-A-0 707 462. In that device, an endoprosthesis is mounted coaxially on two hollow supports capable of sliding relative to each other. The endoprosthesis is maintained in its retracted state by means of two filamentary connections surrounding it at its ends. The filamentary connections are passed into distal and proximal retention openings, respectively, provided in the one and the other of the supports, respectively. The connections are engaged around a retention rod in order to keep them in position at their proximal end.

In order to release the endoprosthesis, the supports are displaced by sliding relative to each other in such a manner that the distance between the retention openings decreases.

The decrease in this distance brings about the loosening of the filamentary connections and consequently the simultaneous deployment of the two ends of the endoprosthesis.

When the positioning of the endoprosthesis in the blood circulation canal is satisfactory, the rod for retaining the filamentary connections is removed from the device. The filamentary connections are then withdrawn from the supports and removed from the patient's body by causing them to slide in the supports.

Bearing in mind the great length of the filamentary connections, and their winding path in the supports, the risk of the filamentary connections becoming jammed or breaking during their withdrawal is high. The reliability of the device is therefore reduced.

SUMMARY OF THE INVENTION

The object of the invention is therefore to propose a device for treating a blood circulation canal, which device can be positioned in a precise manner in the vessel while being simple and reliable to use.

To that end, the invention relates to a treatment device of the above-mentioned type, wherein the retention rod comprises at least one hook for retaining the loop. The displacement of the retention rod from its release position to its retention position brings about the tightening of the clamping ring from its configuration for deploying the endoprosthesis to its configuration for maintaining the endoprosthesis.

The device according to the invention may comprise one or more of the following features, taken in isolation or in accordance with any technically possible combination:

the hook is placed at a distal end of the retention rod;
the hook delimits, on the retention rod, a distal section of non-zero length and a proximal section, the hook projecting transversely relative to the distal section and to the proximal section;
the endoprosthesis delimits, for each filamentary connection, a guide passage for the filamentary connection, the ends of the clamping ring being engaged in the guide passage;
each filamentary connection is a strand which is closed on itself, the loop being formed by an extension of the clamping ring extending from the guide passage between the ends of the clamping ring;
each filamentary connection is mounted permanently on the endoprosthesis;
the support delimits a proximal retention opening and a distal retention opening, the device comprising, for each retention opening, a separate retention rod comprising a retention hook;
the support delimits a proximal retention opening and a distal retention opening, the device comprising a common retention rod comprising a distal hook and a proximal hook;
the endoprosthesis is mounted coaxially on the support;
each filamentary connection is releasable from the endoprosthesis, the retention rod comprising means for retaining at least one retention section of the filamentary connection which is separate from the loop, the section being retained by the retention means when the loop is released from the retention hook, in order to permit the joint displacement of the filamentary connection and the retention rod; and
the retention section of the filamentary connection forms an auxiliary loop engaged in the support through a retention opening, the retention rod comprising an auxiliary hook for retaining the auxiliary loop, which hook opens proximally relative to the hook for retaining the loop.

The invention relates also to a process for preparing a device such as described above, before it is implanted in a blood circulation canal. The method comprises the following steps: preservation of the endoprosthesis in its expanded state, each loop being engaged in a hook of a rod for retaining the loop; and displacement of the retention rod from its release position to the position for retaining the loop, in order to bring about the tightening of the clamping ring and to bring the endoprosthesis into its retracted state.

BRIEF DESCRIPTION OF THE DRAWINGS

The invention will be better understood upon reading the following description which is given purely by way of example and with reference to the appended drawings in which.

DETAILED DESCRIPTION OF THE PREFERRED EMBODIMENTS

The treatment device shown in FIGS. 1 to 5 comprises a tubular endoprosthesis 11 which has a longitudinal axis X-X' and which is mounted coaxially on a single support 13 and is connected to that support 13 by releasable retention means.

The endoprosthesis 11 comprises a tubular trellis of stainless steel which has spring-like properties. Thus, this endoprosthesis expands automatically.

The endoprosthesis 11 is, for example, produced by braiding a single thread of a super-resilient material, as described in European Patent Application EP-A-0 857 471.

The trellis of the endoprosthesis 11 defines, in the vicinity of a distal end 15 of the endoprosthesis 11, a distal guide passage 16A for the retention means, and, in the vicinity of a proximal end 17 of the endoprosthesis 11, a proximal guide passage 17A for the retention means.

Figures 5, 6:
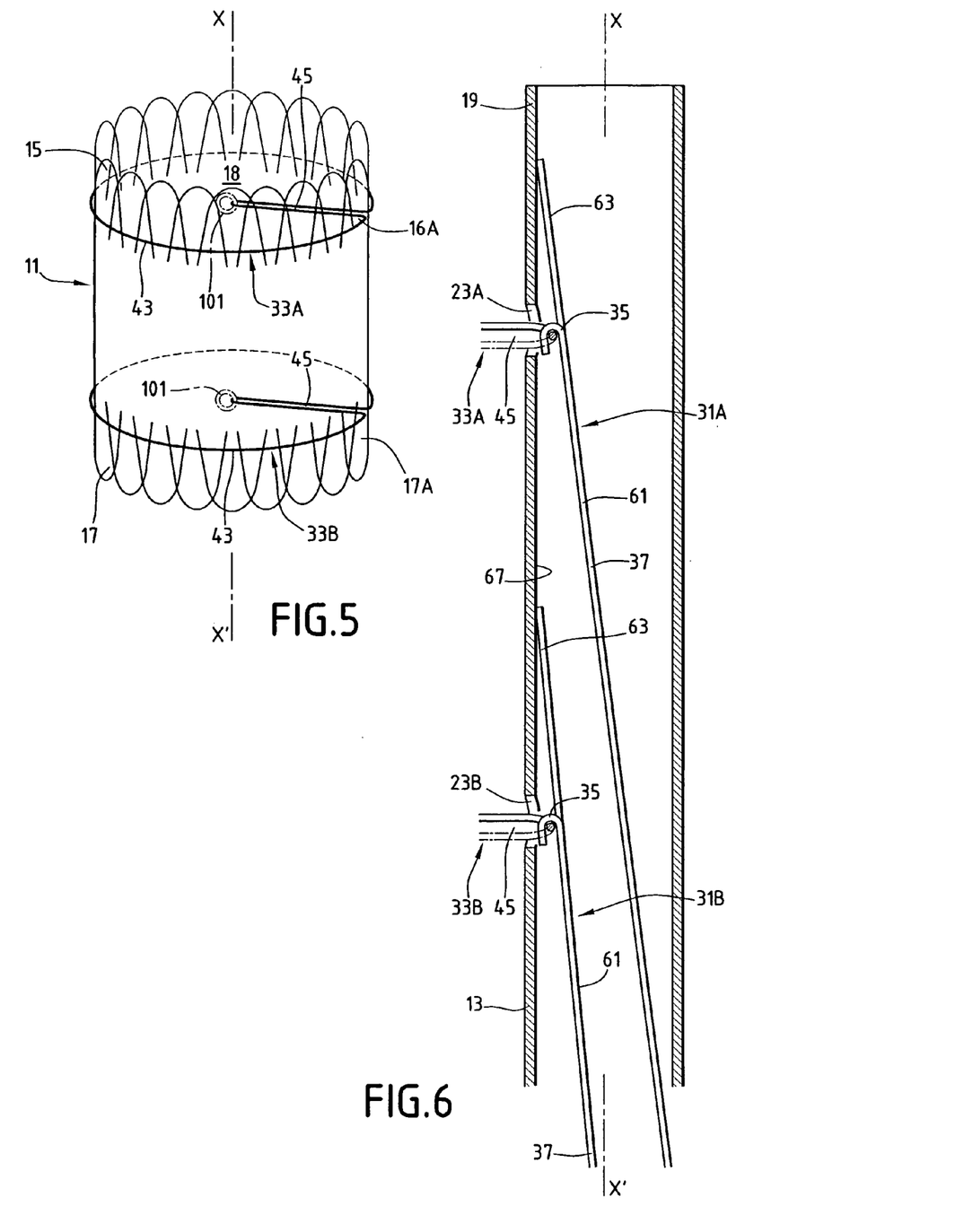
FIG. 5 is a three-quarter perspective view, from the front, of the endoprosthesis of the device of FIG. 1 in its expanded state.
FIG. 6 is a view analogous to FIG. 2 of a detail of a second treatment device according to the invention.

As illustrated by FIG. 5, each guide passage 16A, 17A is delimited by a mesh of the endoprosthesis trellis. The passages 16A, 17A are located on the same longitudinal generatrix of the endoprosthesis 11.

The trellis has, at the ends 15, 17 of the endoprosthesis 11, folded threads forming bends.

The endoprosthesis 11 delimits internally a blood circulation canal 18 having an axis X-X'.

In a variant, the passages 16A, 17A are delimited by annuli which are fixedly joined to the trellis and which are located in the canal 18.

As known per se, the endoprosthesis 11 is capable of changing shape spontaneously from a retracted state in which it has a small diameter (FIG. 1) into an expanded state in which it has a larger diameter (FIG. 5), this expanded state constituting its resting state.

Figure 1:
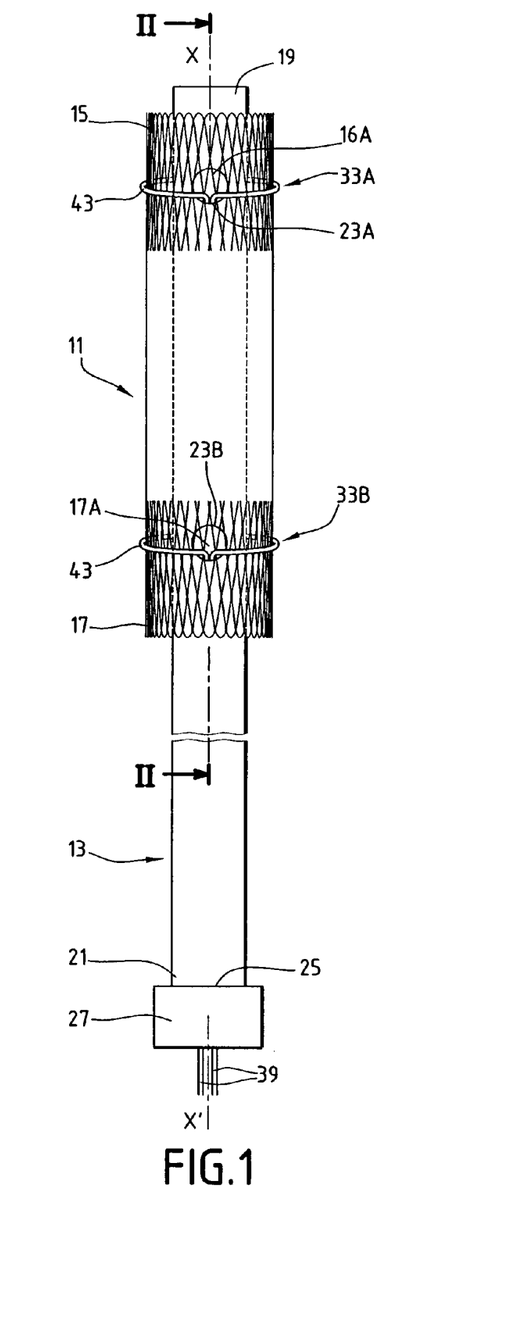
FIG. 1 is a front view of a first treatment device according to the invention, the endoprosthesis being maintained in its retracted state.
Figure 2:
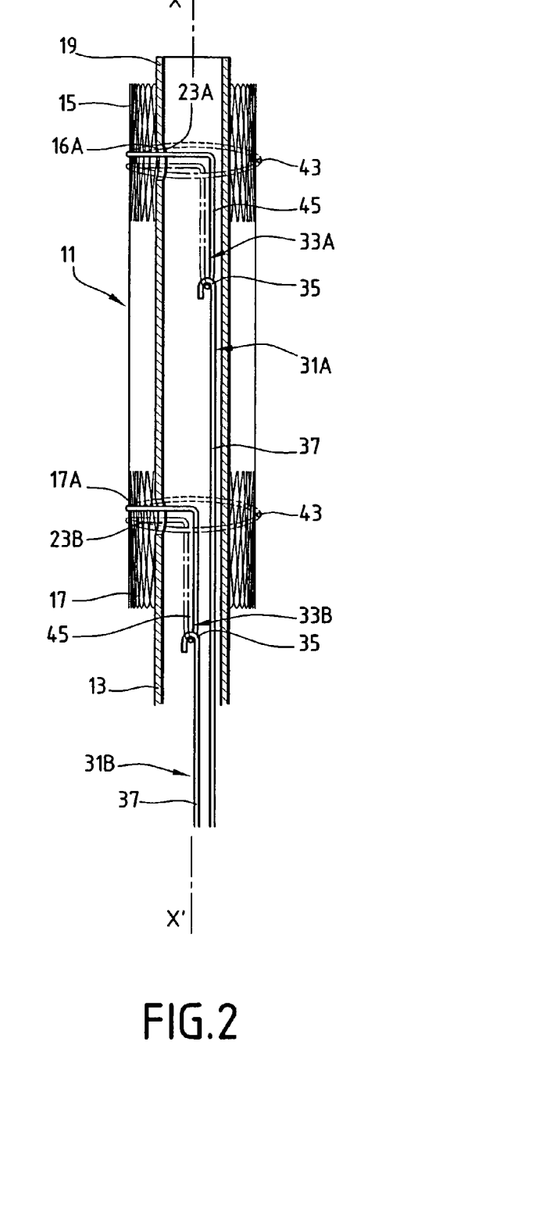
FIG. 2 is a sectioned view, taken on the center transverse plane II-II, of a detail of FIG. 1.

In the example illustrated in FIGS. 1 and 2, the support 13 comprises a hollow flexible metal tube having a longitudinal axis X-X'. The inside diameter of the tube is suitable for enabling the tube to be threaded onto a filamentary surgical guide (not shown) installed in the patient, before the endoprosthesis 11 is put in place in a blood circulation canal of this patient.

The support 13 extends longitudinally in a single piece between a distal end 19 which is to be implanted in the blood circulation canal and a proximal end 21 which is to be accessible to a surgeon. The proximal end 21 is located at a distance from the endoprosthesis 11.

Distal and proximal retention openings 23A and 23B, which are offset longitudinally, are provided laterally in (i.e., in a lateral side of) the support 13, in the vicinity of the distal end 19 of the support 13.

In this example, the openings 23A and 23B are provided on the same side relative to a center longitudinal plane of the support 13. The distance separating the distal retention opening 23A from the proximal retention opening 23B is substantially equal to the length of the endoprosthesis 11 in its retracted state, viewed in a longitudinal direction.

At its proximal end 21, the support 13 delimits a control passage 25 which is closed selectively by locking member 27 for locking a retention device in position.

The retention device of the endoprosthesis 11 comprises a distal retention rod 31A and a proximal retention rod 31B which are associated with a distal retention thread 33A and a proximal retention thread 33B, respectively.

The distal retention rod 31A and the proximal retention rod 31B have similar structures. Likewise, the distal retention thread 33A and the proximal retention thread 33B have similar structures. Consequently, only the distal retention thread 33A and the distal retention rod 31A will be described hereinafter.

The retention rod 31A is located in the support 13. The length of the rod 31A is greater than or equal to the distance between the distal retention opening 23A and the proximal end 21 of the support 13.

As illustrated in FIG. 2, the rod 31A comprises an end hook 35, a straight actuating portion 37, and a straight control section 39 which projects through the control passage 25 at the proximal end 21 of the support 13. The retention rod 31A thus has the general shape of a crook, including a straight main portion (the control section 39 and actuating section 37) and an end hook 35 at the distal end thereof.

The end hook 35 is located at the distal end of the actuating portion 37. It projects laterally relative to the actuating portion 37 towards the distal retention opening 23A.

The actuating portion 37 is produced from of a flexible metal rod. It extends in the support 13.

The control section 39 extends the actuating portion 37 outside the support 13, through the control passage 25.

Figures 3, 4:
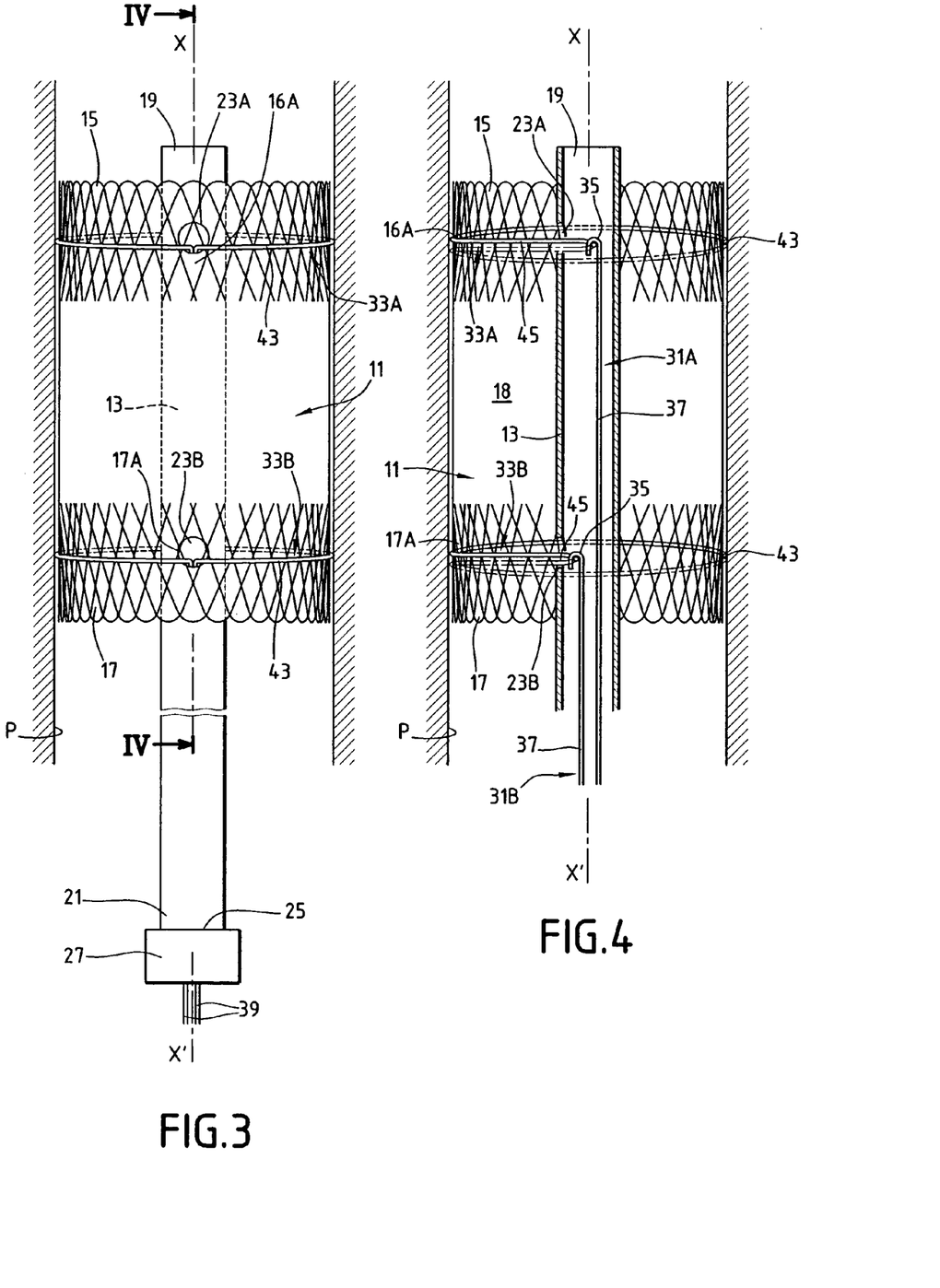
FIG. 3 is a view analogous to FIG. 1, the endoprosthesis being in its expanded state.
FIG. 4 is a view analogous to FIG. 2 of the endoprosthesis of FIG. 3.

The rod 31A is movable in translation along the longitudinal axis X-X' of the support 13, between a distal position shown in FIG. 4 for releasing the retention thread 33A and a proximal position shown in FIG. 2 for traction on the retention thread 33A.

In the distal release position, the hook 35 extends (is positioned) substantially opposite the distal retention opening 23A. In that position, the control section 39 has a minimum length.

In the proximal traction position, the hook 35 is located between the proximal retention opening 23B and the distal retention opening 23A. The length of the control section 39 is therefore at a maximum.

In the example shown in FIGS. 1 to 5, the distal retention thread 33A comprises a single strand of pliable material closed on itself (i.e., in a loop). The distal retention thread 33A thus forms a clamping ring portion 43 located outside the support 13 in order to surround the endoprosthesis 11, and a constricting loop portion 45 engaged in the support 13 through the distal retention opening 23A.

The distal retention thread 33A is mounted permanently on the endoprosthesis 11.

The clamping ring 43 surrounds the endoprosthesis 11 outside an entirety of a circumference of an outer surface of the trellis, in accordance with a circumference around the axis X-X'. It extends between a first end and a second end which are engaged in the proximal guide passage 16A and which are connected to the loop 45.

In a variant, the clamping ring portion 43 is engaged in the trellis of the endoprosthesis 11, in accordance with a circumference, by passing in succession to the inside and to the outside of the trellis.

The constricting loop portion 45 extends in the support 13 by connecting the two ends of the clamping ring portion 43 through the retention opening 23A. The constricting loop portion 45 is engaged in the hook 35 of the retention rod 31A (i.e., the hook 35 engages the constricting loop portion 45).

The clamping ring portion 43 is extensible between a configuration for maintaining the endoprosthesis 11 in its retracted state and a configuration for deploying the endoprosthesis 11.

In the configuration for maintaining shown in FIG. 2, the diameter of the clamping ring portion 43 is at a minimum, while the length of the loop portion 45 in the support 13 is at a maximum.

Conversely, as shown in FIG. 4, when the clamping ring portion 43 occupies its deployment configuration, its diameter is at a maximum, while the length of the constricting loop portion 45 in the support 13 is at a minimum.

When the clamping ring portion 43 occupies its configuration for constricting the endoprosthesis 11, the endoprosthesis 11 is maintained in its retracted state against the support 13, along a peripheral lateral surface of the support 13. Conversely, when the clamping ring portion 43 occupies its deployment configuration, the endoprosthesis 11 is free to occupy its expanded state.

The operation of the first treatment device according to the invention will now be described by way of example.

In a first stage, the device is preserved in a sterile pack (not shown).

In the pack, each retention rod 31 substantially occupies its position for releasing the constricting loop portion 45, in which position the hook 35 is located opposite the retention opening 23A, 23B.

For each thread 33A, 33B, the constricting loop portion 45 remains engaged in an associated hook 35, so that the retention rod 31A, 31B retains the retention thread 33A, 33B.

The distal and proximal retention threads 33A and 33B are engaged around the trellis of the endoprosthesis 11, so that each clamping ring 43 occupies its deployment configuration. The endoprosthesis 11 is thus maintained in its expanded state.

In this condition, the mechanical properties of the endoprosthesis 11 are preserved and, in particular, the tubular trellis thereof is embedded in an extensible and leak-tight film, such as an elastomer.

In a second stage, the surgeon implants a surgical guide (not shown) which moves in the blood circulation canal or the vein from the external point of introduction as far as the region of the vein or the artery into which the tubular endoprosthesis 11 is to be implanted.

The surgeon then removes the device from its pack with a view to implanting the endoprosthesis 11 in the blood circulation canal or the vein. The surgeon subsequently releases the locking member 27 for locking the rods 31A, 31B and pulls on the control sections 39 of the retention rods 31A, 31B in order to increase the length of those sections 39.

During this displacement, each hook 35 is displaced towards the proximal end 21 of the support 13 until the retention rods 31A, 31B occupy their position for retaining the loop.

During this displacement, each retention rod 31A, 31B pulls on a corresponding retention thread 33A, 33B. The length of each constricting loop portion 45 increases and the diameter of the clamping ring portions 43 decreases in a corresponding manner. The endoprosthesis 11 thus passes from its expanded state to its retracted state against a peripheral lateral surface of the support 13, in which state the trellis is substantially resting against the support 13, around that support 13. The support 13 is then positioned in the circulation canal 18.

The surgeon then activates the locking member 27 for locking the retention rods 31A, 31B in position in order to immobilize the rods 31A, 31B relative to the support 13.

The endoprosthesis 11 is thus introduced coaxially with the support 13 as far as its place of implantation by displacement along the surgical guide (not shown).

In some cases, and in order to maintain a minimum radial space requirement, a sheath (not shown) is arranged around the endoprosthesis 11, before this introduction, and is withdrawn once the introduction has been carried out.

Once the endoprosthesis 11 has been introduced, the surgeon proceeds with the deployment thereof.

Depending on the conformation of the blood circulation canal to be treated, he may choose to deploy first the one or the other of (i.e., a particular one of) the ends 15 and 17 of the endoprosthesis 11.

The deployment of the distal end 15 will be described by way of example.

First of all, the surgeon releases selectively the control section 39 of the distal retention rod 31A. Then he progressively reduces the length of that section 39 by displacing the rod 31A towards the distal end 19 of the support 13, which displaces the hook 35 towards the distal end 19.

During this displacement, the length of the constricting loop portion 45 decreases. The diameter of the clamping ring portion 43 increases in a corresponding manner, which enables the endoprosthesis 11 to be deployed radially relative to the axis X-X' of the support 13 at the distal end 15 of the endoprosthesis 11. The trellis therefore moves away from the support 13 and approaches the walls P of the canal to be treated in order to rest on those walls P.

If the surgeon is not satisfied with the positioning of the distal end 15 of the endoprosthesis 11 when the latter is deployed, he again actuates the control section 39 by displacing the retention rod 31A towards the proximal end 21 of the support 13. This increases the length of the constricting loop portion 45 and reduces the active size of the clamping ring portion 43 in order to compress the endoprosthesis 11 against the support 13. The endoprosthesis 11 is then displaced until it reaches a more satisfactory position.

In an analogous manner, the surgeon then carries out the deployment of the proximal end 17 of the endoprosthesis 11 by the proximal retention thread 33B.

In this configuration, the retention rods 31A, 31B occupy their position for releasing the constricting loop portion 45. The loop portion 45, however, remain engaged in the hooks 35.

When the surgeon is satisfied with the positioning of the distal end 15 of the endoprosthesis 11, he displaces the distal retention rod 31A towards the distal end 19 of the support 13 in order to bring the hook 35 beyond the distal retention opening 23A until the constricting loop portion 45 is completely released from the hook 35.

The distal end 15 of the endoprosthesis 11 is then secured irreversibly to the walls P of the blood circulation canal.

The surgeon then proceeds in the same manner with the proximal end 17 of the endoprosthesis 11. He subsequently removes the support 13 and the retention rods 31A, 31B from the patient. The support 13 is then completely released from the endoprosthesis 11.

In this device, the length of the retention threads 31A, 31B is at a minimum, so that their movement in the support 13 presents a low risk of blocking.

Consequently, the reliability of the deployment of the endoprosthesis is improved since it is no longer necessary to cause long lengths of thread to move in the support 13.

In a variant shown with a dotted line in FIG. 5, each constricting loop portion 45 has an end annulus 101, which is produced, for example, from a radio-opaque material and which is to be gripped by a hook 35.

In the second device according to the invention, which is shown in FIG. 6, the hook 35 of each retention rod 31A, 31B is not located at the distal end of the rod 31A, 31B.

Thus, each hook 35 delimits on the rod 31A, 31B a proximal section 61 and a distal section 63 of non-zero length, which is suitable for retaining the hook 35 in the support 13.

The hook 35 projects radially relative to the proximal section 61 and to the distal section 63.

When the retention rod 31A, 31B is placed in its position for releasing the constricting loop portion 45, with the hook 35 located opposite a retention opening 23A, 23B, the distal section 63 rests against the internal surface 67 of the support 13, distally relative to the opening 23A, 23B. This prevents the hook 35 from being carried along by the loop 45 out of the support 13 through the retention opening 23A, 23B during the deployment of the endoprosthesis 11. The reliability of the device is further improved.

In a variant (not shown), the two retention rods 31A, 31B are connected mechanically at a point located proximally relative to the proximal retention opening 23B when the hooks 35 are located opposite the retention openings 23A, 23B.

Figure 7:
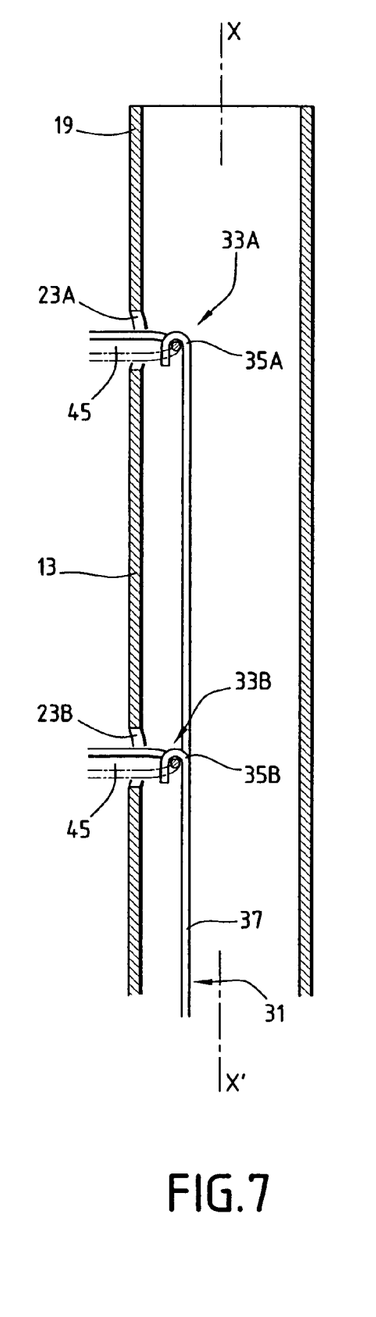
FIG. 7 is a view analogous to FIG. 6 of a third device according to the invention.

The third device according to the invention, which is shown in FIG. 7, comprises a single retention rod 31 which is provided with a distal retention hook 35A located at the distal end of the rod 31, and with a proximal retention hook 35B which projects relative to the rod 31.

The distance separating the distal hook 35A from the proximal hook 35B is substantially equal to the distance separating the distal retention opening 23A from the proximal retention opening 23B.

This third device permits the simultaneous deployment of the proximal end 17 and the distal end 15 of the endoprosthesis 11.

Figure 8:
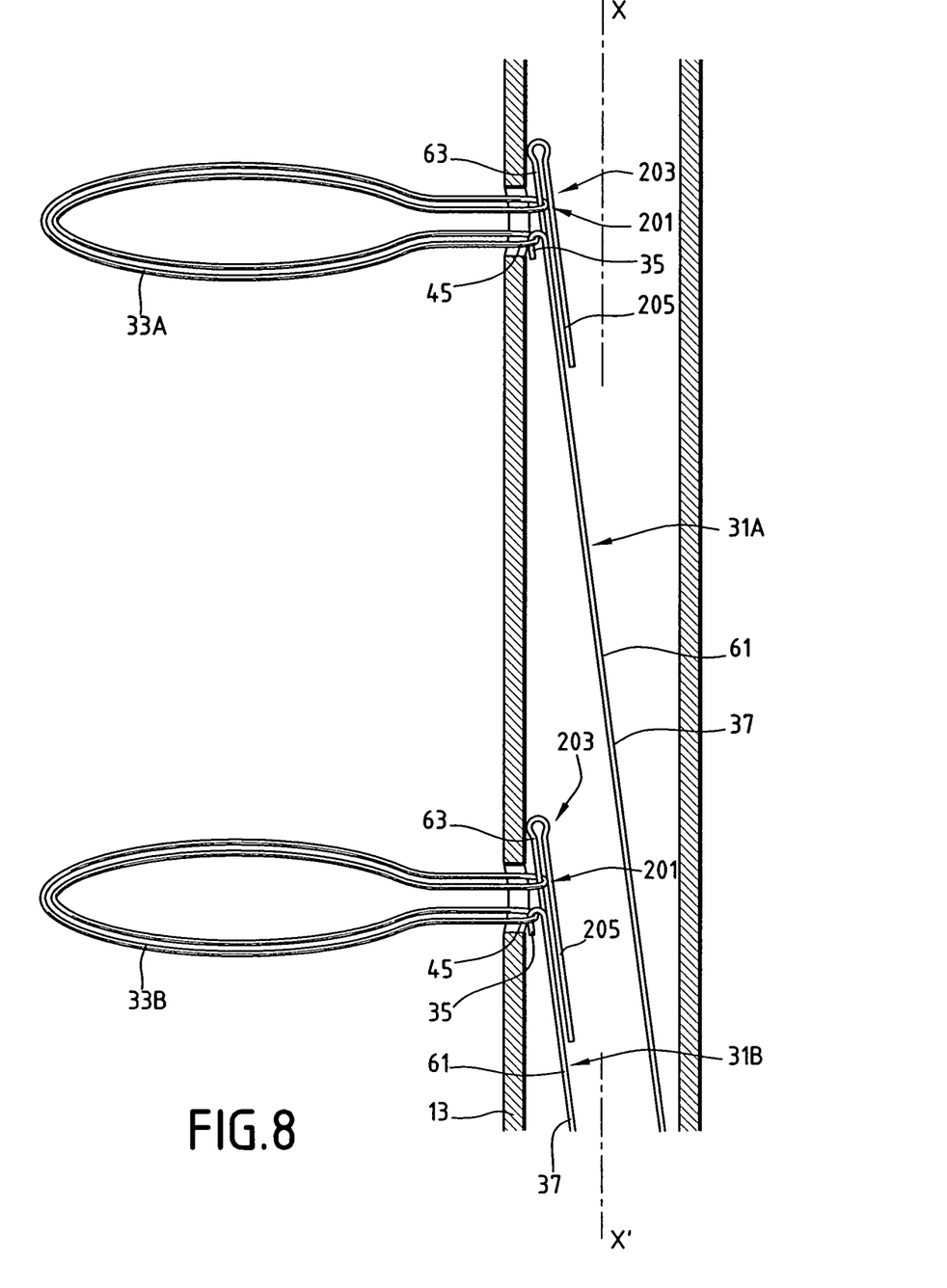
FIG. 8 is a view analogous to FIG. 6 of a fourth device according to the invention, the endoprosthesis not being shown.
Figure 9:
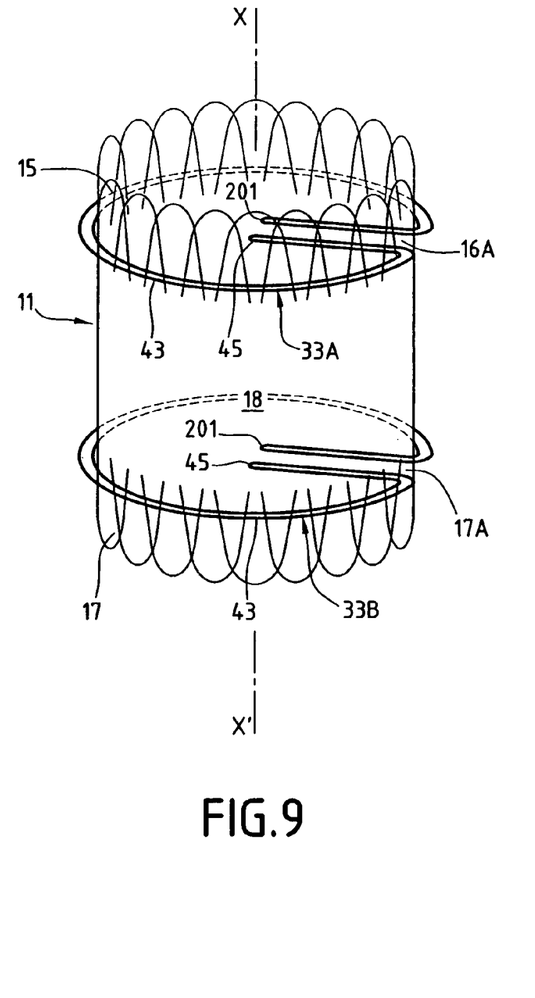
FIG. 9 is a view analogous to FIG. 5 of the endoprosthesis of the device of FIG. 8.

A fourth device according to the invention is shown in FIGS. 8 and 9. This device constitutes a variant of the second treatment device according to the invention. However, unlike the second device, each retention thread 33A, 33B is releasable from the endoprosthesis 11.

To that end, each retention thread 33A, 33B forms a principal constricting loop portion 45 connected to a first end of the clamping ring 43, and an auxiliary loop portion 201 located in the support 13 and connected to a second end of the clamping ring portion 43.

The clamping ring portion 43 is formed by two adjacent strands of the retention thread 33A, 33B. These two strands are folded into a loop at the first end of the clamping ring portion 43 in order to form the principal constricting loop portion 45 and are folded into a loop at the second end of the clamping ring portion 43 in order to form the auxiliary loop portion 201.

The principal constricting loop portion 45 and the auxiliary loop portion (retention portion) 201 are connected to the clamping ring portion 43 through the same retention opening 23A, 23B and through the same guide passage 16A, 17A.

Unlike the device shown in FIG. 6, each retention rod 31A, 313 has at its distal end a clip retaining member) 203 for retaining the auxiliary loop portion (retention portion) 201.

The clip 203 is formed by a fold 205 in the distal section 63 of the retention rod 31A, 31B extending between the distal end of the rod 31A, 31B as far as a point located proximally relative to the retention hook 35. The fold 205 extends in the opposite direction to the hook 35 and the retention opening 23A, 23B, relative to the axis of the rod 31A, 31B. The clip 203 opens towards the proximal end 21 of the support 13.

The auxiliary loop portion 201 is engaged in the retention clip 203.

When the surgeon removes the fourth device from its pack and displaces each retention rod 31A, 31B towards the proximal end 21 of the support 13, the hook 35 and the clip 203 of each rod 31A, 31B also move towards that proximal end.

During this displacement, the loop 45 and the auxiliary loop portion 201 are pulled in the support 13 towards the proximal end 21, so that the length of the clamping ring portion 43 decreases in order to cause the endoprothesis 11 to pass from its expanded state into its retracted state against the support 13.

The deployment of the endoprosthesis 11 is then analogous to that of the second treatment device.

When the endoprosthesis 11 is deployed in position in the blood circulation canal and the surgeon is satisfied with the positioning of this endoprosthesis, he displaces the retention rod 31A, 31B towards the distal end 19 of the support 13 in order to bring the hook 35 beyond the corresponding retention opening 23A, 23B. The principal constricting loop portion 45 is then completely released from the hook 35.

However, bearing in mind the length of the fold 205, the auxiliary loop portion 201 remains engaged in the clip 203.

Subsequently, when the surgeon pulls the retention rod 31A, 31B towards the proximal end 21 of the support 13, he also pulls on the corresponding retention thread 33A, 33B by way of the auxiliary loop portion 201 engaged in the clip 203 in order to permit the joint displacement of the retention thread 33A, 33B and the retention rod 31A, 31B. The retention thread 33A, 33B is then completely released from the endoprosthesis 11 and is removed from the patient at the same time as the retention rod 31A, 31B.

The invention claimed is:

1. A device for treating a blood circulation canal, comprising:
   a hollow support having a distal end and a proximal end, and having a transverse distal retention opening at said distal end;
   an endoprosthesis configured to be deployed in both a retracted state, wherein said endoprosthesis is retracted against a lateral surface of said support, and an expanded state, wherein said endoprosthesis is released from said support;
   a filamentary connection having:
     a clamping ring portion surrounding an entirety of a circumference of an outer surface of said endoprosthesis, said clamping ring portion located outside of said hollow support and having a first end and a second end extending into said hollow support through said retention opening; and a constricting loop portion having a first end and a second end connected to said first end and said second end, respectively, of said clamping ring portion such that said constricting loop portion is located entirely within said hollow support without protruding from said hollow support, said clamping ring portion being interchangeable between a retracted configuration for constricting and maintaining said endoprosthesis in the retracted state, and an expanded configuration for deploying said endoprosthesis; and a retention rod mounted so to be movable within said support between a retain position for retaining and pulling said constricting loop portion and a release position for releasing said constricting loop portion, said retention rod comprising a hook for engaging and retaining said constricting loop portion of said filamentary connection;

wherein said endoprosthesis, said filamentary connection, and said retention rod are arranged and interconnected such that movement of said retention rod from the release position to the retain position causes tightening of said clamping ring portion of said filamentary connection by changing a configuration of said clamping ring portion from the expanded configuration for deploying said endoprosthesis to the refracted configuration for constricting and maintaining said endoprosthesis in the retracted state; and wherein said endoprosthesis, said filamentary connection, and said retention rod are arranged and interconnected such that movement of said retention rod from the release position to the retain position causes an increase in size of said constricting loop portion and a corresponding reduction in size of said clamping ring portion.

2. The device of claim 1, wherein said hook is at a distal end of said retention rod.

3. The device of claim 1, wherein said hook is positioned on said retention rod between a distal section of said retention rod having a first length of a non-zero value and a proximal section of said retention rod having a second length of non-zero value, said hook projecting transversely relative to said distal section and said proximal section.

4. The device of claim 1, wherein said endoprosthesis is shaped to form a guide passage for said filamentary connection, said first end and said second end of said clamping ring portion being engaged in said guide passage.

5. The device of claim 4, wherein said filamentary connection is a closed strand, said constricting loop portion being formed as an extension of said clamping ring portion extending through said guide passage between and from said first end and said second end of said clamping ring portion.

6. The device of claim 1, wherein said filamentary connection is permanently mounted to said endoprosthesis.

7. The device of claim 1, wherein said support has a proximal retention opening and said distal retention opening, said retention rod comprising a first retention rod interacting with said distal retention opening, said device further comprising a separate second retention rod comprising a retention hook interacting with said proximal retention opening.

8. The device of claim 1, wherein said support has a proximal retention opening and said distal retention opening, said retention rod comprising a common retention rod interacting with both said proximal retention opening and said distal retention opening, said hook comprising a distal hook interacting with said distal retention opening, said common retention rod further comprising a proximal hook interacting with said proximal retention opening.

9. The device of claim 1, wherein said endoprosthesis is mounted coaxially on said support.

10. The device of claim 1, wherein said filamentary connection is releasable from said endoprosthesis, said retention rod comprising a retaining member for retaining a retention portion of said filamentary connection, said retention portion being separate from said constricting loop portion, said retention portion being retained by said retention member when said constricting loop portion is released from said hook so as to allow said filamentary connection to be removed from said endoprosthesis with said retention rod.

11. The device of claim 10, wherein said retention portion of said filamentary connection forms an auxiliary loop portion extending into said support through said distal retention opening, said retention member of said retention rod comprising an auxiliary hook for retaining said auxiliary loop portion, an opening of said auxiliary hook being located closer to a proximal end of said retention rod than is an opening of said hook for engaging and retaining said constricting loop portion.

12. The device of claim 1, wherein said filamentary connection comprises a first filamentary connection at a distal end of said endoprosthesis, further comprising a second filamentary connection at a proximal end of said endoprosthesis, said support having said distal retention opening and a proximal retention opening, each of said first filamentary connection and said second filamentary connection having a clamping ring portion and having a constricting loop portion extending through a respective one of said distal retention opening and said proximal retention opening.

13. A device for treating a blood circulation canal, comprising:

a hollow support having a distal end and a proximal end, and having a transverse distal retention opening at said distal end;

an endoprosthesis configured to be deployed in both a retracted state, wherein said endoprosthesis is retracted against a lateral surface of said support, and an expanded state, wherein said endoprosthesis is released from said support;

a filamentary connection having a clamping ring portion surrounding an entirety of a circumference of an outer surface of said endoprosthesis, and having a constricting loop portion extending into said support through said retention opening, said clamping ring portion being interchangeable between a retracted configuration for constricting and maintaining said endoprosthesis in the retracted state, and an expanded configuration for deploying said endoprosthesis;

a retention rod mounted so to be movable within said support between a retain position for retaining and pulling said constricting loop portion and a release position for releasing said constricting loop portion, said retention rod comprising a hook for engaging and retaining said constricting loop portion of said filamentary connection; and a locking member for locking a control section of said retention rod to prevent movement of said retention rod, said control section being located at a proximal end of said retention rod, and said locking member being located at a proximal end of said support;

wherein said endoprosthesis, said filamentary connection, and said retention rod are arranged and interconnected such that movement of said retention rod from the release position to the retain position causes tightening of said clamping ring portion of said filamentary connection by changing a configuration of said clamping ring portion from the expanded configuration for deploying said endoprosthesis to the refracted configuration for constricting and maintaining said endoprosthesis in the retracted state; and wherein said endoprosthesis, said filamentary connection, and said retention rod are arranged and interconnected such that movement of said retention rod from the release position to the retain position causes an increase in size of said constricting loop portion and a corresponding reduction in size of said clamping ring portion.

14. A method of preparing the device of claim 1 before the device is implanted in the blood circulation canal, said process comprising:

preserving the endoprosthesis in the expanded state, the constricting loop portion being engaged in the hook of the retention rod positioned in the release position;

moving the retention rod from the release position to the retain position so as to tighten the clamping ring portion by changing the clamping ring portion from the expanded configuration to the retracted configuration and thereby bring the endoprosthesis into the refracted state.

15. The device of claim 1, wherein said filamentary connection consists of a single strand formed as a continuous closed loop without any free ends.

16. The device of claim 13, wherein said filamentary connection consists of a single strand formed as a continuous closed loop without any free ends.

* * * * *